(12) United States Patent
Hunt et al.

(10) Patent No.: US 9,221,743 B2
(45) Date of Patent: Dec. 29, 2015

(54) TRIPHENYL MONOMERS SUITABLE FOR MICROSTRUCTURED OPTICAL FILMS

(71) Applicant: 3M INNOVATIVE PROPERTIES COMPANY, St. Paul, MN (US)

(72) Inventors: Bryan V. Hunt, Nowthen, MN (US);
Kyle J. Lindstrom, Houlton, WI (US);
Judith M. Invie, Woodbury, MN (US);
David B. Olson, Marine on St. Croix, MN (US); Anthony M. Renstrom, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/503,459

(22) Filed: Oct. 1, 2014

(65) Prior Publication Data
US 2015/0141692 A1    May 21, 2015

Related U.S. Application Data

(62) Division of application No. 14/022,375, filed on Sep. 10, 2013, now Pat. No. 8,871,315, which is a division of application No. 12/528,636, filed as application No. PCT/US2008/055654 on Mar. 3, 2008, now Pat. No. 8,586,154.

(60) Provisional application No. 60/948,611, filed on Jul. 9, 2007, provisional application No. 60/893,953, filed on Mar. 9, 2007.

(51) Int. Cl.
| | |
|---|---|
| *C09K 19/00* | (2006.01) |
| *C07C 69/78* | (2006.01) |
| *C08F 32/06* | (2006.01) |
| *G02B 1/10* | (2015.01) |
| *C07C 43/23* | (2006.01) |
| *C07C 69/734* | (2006.01) |

(52) U.S. Cl.
CPC .............. *C07C 69/78* (2013.01); *C07C 43/23* (2013.01); *C07C 69/734* (2013.01); *C08F 32/06* (2013.01); *G02B 1/10* (2013.01); *Y10T 428/10* (2015.01); *Y10T 428/105* (2015.01); *Y10T 428/1036* (2015.01); *Y10T 428/1041* (2015.01)

(58) Field of Classification Search
CPC .......... G02B 1/10; G02B 1/105; C08F 32/06; C08F 32/04; Y10T 428/1036; Y10T 428/105
USPC .................. 524/560, 558; 526/327, 328, 326; 428/1.3, 1.33
See application file for complete search history.

(56) References Cited

U.S. PATENT DOCUMENTS

| | | | |
|---|---|---|---|
| 4,458,006 | A | 7/1984 | Doenges et al. |
| 4,518,756 | A | 5/1985 | Yoshida et al. |
| 4,576,850 | A | 3/1986 | Martens |
| 4,650,719 | A | 3/1987 | Dien et al. |
| 5,169,915 | A | 12/1992 | Mohri |
| 5,183,917 | A | 2/1993 | Maruyama et al. |
| 5,334,681 | A | 8/1994 | Mueller et al. |
| 5,453,452 | A | 9/1995 | Nakayama et al. |
| 5,629,445 | A | 5/1997 | Nakayama et al. |
| 5,716,740 | A | 2/1998 | Shiba et al. |
| 6,458,908 | B1 | 10/2002 | Imai et al. |
| 7,074,463 | B2 | 7/2006 | Jones et al. |
| 7,309,517 | B2 | 12/2007 | Jones et al. |
| 7,524,543 | B2 | 4/2009 | Jones et al. |
| 7,622,164 | B2 | 11/2009 | Jones et al. |
| 2002/0123589 | A1 | 9/2002 | Olson et al. |
| 2005/0059766 | A1 | 3/2005 | Jones et al. |
| 2005/0148735 | A1 | 7/2005 | Olson |
| 2006/0004166 | A1 | 1/2006 | Olson |
| 2006/0128853 | A1 | 6/2006 | Olson |
| 2006/0132945 | A1 | 6/2006 | Sano |
| 2006/0210726 | A1 | 9/2006 | Jones |
| 2006/0261318 | A1 | 11/2006 | Morimoto |
| 2008/0221291 | A1 | 9/2008 | Invie et al. |
| 2009/0047486 | A1 | 2/2009 | Jones et al. |
| 2009/0176061 | A1 | 7/2009 | Jones et al. |
| 2009/0246417 | A1 | 10/2009 | Jones et al. |

FOREIGN PATENT DOCUMENTS

| | | |
|---|---|---|
| CN | 1902246 | 1/2007 |
| EP | 0109073 | 5/1984 |
| EP | 0126397 | 11/1984 |
| EP | 1057808 | 6/2000 |
| EP | 1455200 | 9/2004 |
| JP | 59-86615 | 5/1984 |
| JP | 61127712 | 6/1986 |
| JP | 7-316245 | 12/1995 |
| JP | 08188625 A * | 7/1996 |

(Continued)

OTHER PUBLICATIONS

Beilstein Institute for Organic Chemistry, Beilstein Registry No. 3557396, © 2007-2008; XP002496691.

(Continued)

*Primary Examiner* — Ruiyun Zhang

(74) *Attorney, Agent, or Firm* — Carolyn A. Fischer

(57) ABSTRACT

Optical films are described having a polymerized microstructured surface that is the reaction product of a polymerizable resin composition comprising at least one polymerizable ethylenically unsaturated triphenyl monomer. Also described are certain triphenyl (meth)acrylate monomers and polymerizable resin compositions.

20 Claims, No Drawings

(56) References Cited

FOREIGN PATENT DOCUMENTS

| | | |
|---|---|---|
| JP | 09-087336 | 3/1997 |
| JP | 09-272707 | 10/1997 |
| JP | 11-116625 | 4/1999 |
| JP | 11-189629 | 7/1999 |
| JP | 2003-026735 | 1/2003 |
| JP | 3397448 | 4/2003 |
| JP | 2004-182702 | 7/2004 |
| JP | 2004-231704 | 8/2004 |
| JP | 2004-323557 | 11/2004 |
| JP | 2005-272773 | 10/2005 |
| JP | 2005-283632 | 10/2005 |
| JP | 2006-308840 | 11/2006 |
| WO | WO 00/34804 | 6/2000 |
| WO | WO 2004/074884 | 9/2004 |
| WO | WO 2005/003822 | 1/2005 |
| WO | WO 2006/007286 | 1/2006 |
| WO | WO 2008/121465 | 10/2008 |

OTHER PUBLICATIONS

Beilstein Institute for Organic Chemistry, Beilstein Registry No. 5994137, © 2007-2008; XP002496692.
Beilstein Institute for Organic Chemistry, Beilstein Registry No. 2917342, © 2007-2008; XP002496693.
Beilstein Institute for Organic Chemistry, Beilstein Registry No. 2922680, © 2007-2008; XP002496694.
63232WO003 Int'l Search Report (PCT/US2008/055654).
Levashova et al.; The Effect of Substituents in the Aromatic Ring of Phenol on the Alkenylation of 3-Chloro-2-Chloromethyl-1-Propene; Journal of Organic Chemistry (1989) pp. 1319-13-21.
Lein et al.; Host-Guest Complexation. 34. Bridged Hemispherands; Journal of the American Chemical Society (1985) pp. 448-455.
Greber et al; Darstellung and Polymerisation von ungesattigten 1,3,5-Triphenylbenzolderivaten; Journal Makromolekulare Chemie; 40, 1960; pp. 1-15.
Trityl Methacrylate Formula, Retrieved from Website Chemical Book, Jan. 2014.

\* cited by examiner

TRIPHENYL MONOMERS SUITABLE FOR MICROSTRUCTURED OPTICAL FILMS

CROSS-REFERENCE TO RELATED APPLICATIONS

This is a divisional application of U.S. Ser. No. 14/022,375, filed Sep. 10, 2013 (allowed) which is a Divisional of Ser. No. 12/528,636, filed Aug. 26, 2009 (issued as U.S. Pat. No. 8,586,154), which is a U.S. national stage filing under 35 U.S.C. 371 of PCT/US08/55654, filed Mar. 3, 2008, which claims the benefit of Provisional Application No. 60/948,611, filed Jul. 9, 2007 and Provisional Application No. 60/893,953, filed Mar. 9, 2007.

BACKGROUND

Certain microstructured optical products, such as described in U.S. Pat. Nos. 5,175,030 and 5,183,597, are commonly referred to as a "brightness enhancing films". Brightness enhancing films are utilized in many electronic products to increase the brightness of a backlit flat panel display such as a liquid crystal display (LCD) including those used in electroluminescent panels, laptop computer displays, word processors, desktop monitors, televisions, video cameras, as well as automotive and aviation displays.

Brightness enhancing films desirably exhibit specific optical and physical properties including the index of refraction of a brightness enhancing film that is related to the brightness gain (i.e. "gain") produced. Improved brightness can allow the electronic product to operate more efficiently by using less power to light the display, thereby reducing the power consumption, placing a lower heat load on its components, and extending the lifetime of the product.

Brightness enhancing films have been prepared from high index of refraction monomers that are cured or polymerized. Halogenated (e.g. brominated) monomers or oligomers are often employed to attain refractive indices of for example 1.56 or greater. Another way to attain high refractive index compositions is to employ a polymerizable composition that comprises high refractive index nanoparticles such as described in U.S. Publication Nos. 2006/0204745, 2006/0210726, 2006/0204676, and US 2006/0128853.

SUMMARY

In one embodiment, optical films and polymerizable resin compositions are described comprising up to 50 wt-% of one or more triphenyl (meth)acrylate monomers; and 25 wt-% to 75 wt-% of one or more di(meth)acrylate monomers or oligomers selected from bisphenol A (meth)acrylates, aromatic epoxy (meth)acrylate, and mixtures thereof.

In other embodiments, optical films are described comprising a polymerized microstructured surface wherein the microstructured surface comprises the reaction product of a polymerizable resin composition comprising at least one triphenyl monomer having the general structure

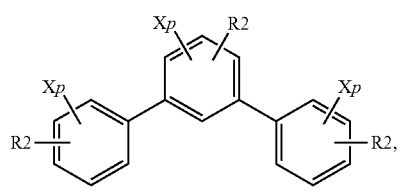

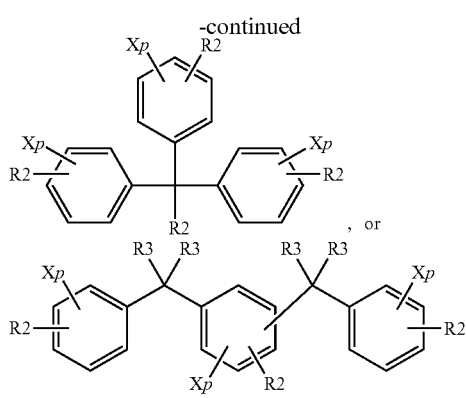

wherein R2 is independently H, methyl, or a substituent comprising a (meth)acrylate group and at least one R2 is a substituent comprising a (meth)acrylate group;

X is independently halogen, aryl, or a $C_2$ to $C_{12}$ alkyl group;

R3 is independently hydrogen, methyl, aryl, or a $C_2$ to $C_{12}$ alkyl group; and and p is 0 to 5.

In another embodiment, an optical film is described comprising a polymerized microstructured surface wherein the polymerized microstructured surface comprises the reaction product of a polymerizable resin composition comprising at least one polymerizable multifunctional ethylenically unsaturated triphenyl monomer.

In yet another embodiment, a triphenyl monomer is described having the general structure

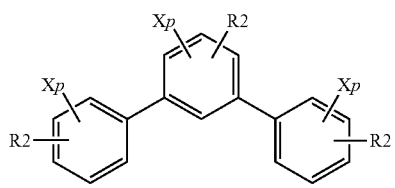

wherein X is independently halogen, aryl, or a $C_2$ to $C_{12}$ alkyl group;

p is 0 to 5; and

R2 is independently H or a substituent comprising a (meth) acrylate group and at least one R2 comprises a substituent comprising a (meth)acrylate group selected from i)

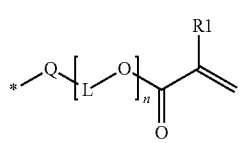

ii)

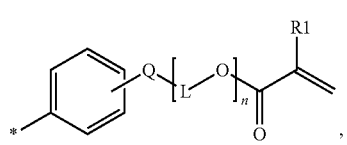

and
wherein Q is O or S;
L is a $C_2$ to $C_6$ alkylene group optionally substituted with a one or more hydroxyl groups;
n ranges from 1 to 10; and
R1 is H or $CH_3$.

DETAILED DESCRIPTION

Presently described are optical films, polymerizable resin compositions, and certain triphenyl (meth)acrylate monomers. The optical films preferably have a polymerized microstructured surface that comprises the reaction product of a polymerizable resin composition comprising at least one polymerizable ethylenically unsaturated triphenyl monomer.

The polymerized microstructure can be an optical element or optical product constructed of a base layer and a polymerized microstructured optical layer. The base layer and optical layer can be formed from the same or different polymeric material. One preferred optical film having a polymerized microstructured surface is a brightness enhancing film.

Brightness enhancing films generally enhance on-axis luminance (referred herein as "brightness") of a lighting device. Brightness enhancing films can be light transmissible, microstructured films. The microstructured topography can be a plurality of prisms on the film surface such that the films can be used to redirect light through reflection and refraction. The height of the prisms typically ranges from about 1 to about 75 microns. When used in an optical display such as that found in laptop computers, watches, etc., the microstructured optical film can increase brightness of an optical display by limiting light escaping from the display to within a pair of planes disposed at desired angles from a normal axis running through the optical display. As a result, light that would exit the display outside of the allowable range is reflected back into the display where a portion of it can be "recycled" and returned back to the microstructured film at an angle that allows it to escape from the display. The recycling is useful because it can reduce power consumption needed to provide a display with a desired level of brightness.

The brightness enhancing film of the invention generally comprises a (e.g. preformed polymeric film) base layer and an optical layer. The optical layer comprises a linear array of regular right prisms. Each prism has a first facet and a second facet. The prisms are formed on base that has a first surface on which the prisms are formed and a second surface that is substantially flat or planar and opposite first surface. By right prisms it is meant that the apex angle is typically about 90°. However, this angle can range from 70° to 120° and may range from 80° to 100°. These apexes can be sharp, rounded or flattened or truncated. For example, the ridges can be rounded to a radius in a range of 4 to 7 to 15 micrometers. The spacing between prism peaks (or pitch) can be 5 to 300 microns. For thin brightness enhancing films, the pitch is preferably 10 to 36 microns, and more preferably 18 to 24 microns. This corresponds to prism heights of preferably about 5 to 18 microns, and more preferably about 9 to 12 microns. The prism facets need not be identical, and the prisms may be tilted with respect to each other. The relationship between the total thickness of the optical article, and the height of the prisms, may vary. However, it is typically desirable to use relatively thinner optical layers with well-defined prism facets. For thin brightness enhancing films on substrates with thicknesses close to 1 mil (20-35 microns), a typical ratio of prism height to total thickness is generally between 0.2 and 0.4.

As described in Lu et al., U.S. Pat. No. 5,175,030, and Lu, U.S. Pat. No. 5,183,597, a microstructure-bearing article (e.g. brightness enhancing film) can be prepared by a method including the steps of (a) preparing a polymerizable composition; (b) depositing the polymerizable composition onto a master negative microstructured molding surface in an amount barely sufficient to fill the cavities of the master; (c) filling the cavities by moving a bead of the polymerizable composition between a preformed base (such as a PET film) and the master, at least one of which is flexible; and (d) curing the composition. The master can be metallic, such as nickel, nickel-plated copper or brass, or can be a thermoplastic material that is stable under the polymerization conditions, and that preferably has a surface energy that allows clean removal of the polymerized material from the master. One or more the surfaces of the base film can optionally be primed or otherwise be treated to promote adhesion of the optical layer to the base.

In some embodiments, the polymerizable resin composition comprises surface modified inorganic nanoparticles. In such embodiments, "polymerizable composition" refers to the total composition, i.e. the organic component and surface modified inorganic nanoparticles. The "organic component" refers to all of the components of the composition except for the surface modified inorganic nanoparticles. Since the surface treatments are generally adsorbed or otherwise attached to the surface of the inorganic nanoparticles, the surface treatments are not considered a portion of the organic component. When the composition is free of inorganic materials such as surface modified inorganic nanoparticles the polymerizable resin composition and organic component are one in the same.

The organic component as well as the polymerizable composition is preferably substantially solvent free. "Substantially solvent free" refer to the polymerizable composition having less than 5 wt-%, 4 wt-%, 3 wt-%, 2 wt-%, 1 wt-% and 0.5 wt-% of non-polymerizable (e.g. organic) solvent. The concentration of solvent can be determined by known methods, such as gas chromatography (as described in ASTM D5403). Solvent concentrations of less than 0.5 wt-% are preferred.

The components of the organic component are preferably chosen such that the polymerizable resin composition has a low viscosity. In some embodiments, the viscosity of the organic component is less than 1000 cps and typically less than 900 cps at the coating temperature. The viscosity of the organic component may be less than 800 cps, less than 700 cps, less than 600 cps, or less than 500 cps at the coating temperature. As used herein, viscosity is measured (at a shear rate up to 1000 sec-1) with 25 mm parallel plates using a Dynamic Stress Rheometer. Further, the viscosity of the organic component is typically at least 10 cps, more typically at least 50 cps at the coating temperature.

The coating temperature typically ranges from ambient temperature, 77° F. (25° C.) to 180° F. (82° C.). The coating temperature may be less than 170° F. (77° C.), less than 160° F. (71° C.), less than 150° F. (66° C.), less than 140° F. (60° C.), less than 130° F. (54° C.), or less than 120° F. (49° C.). The organic component can be a solid or comprise a solid component provided that the melting point in the polymerizable composition is less than the coating temperature. The organic component is preferably a liquid at ambient temperature.

The triphenyl monomer and/or the organic component has a refractive index of at least 1.55, 1.56, 1.57, 1.58, 1.59, or 1.60. The polymerizable composition including high refractive index nanoparticles can have a refractive index as high as 1.70. (e.g. at least 1.61, 1.62, 1.63, 1.64, 1.65, 1.66, 1.67, 1.68, or 1.69) High transmittance in the visible light spectrum is also typically preferred.

The polymerizable composition is energy curable in time scales preferably less than five minutes (e.g. for a brightness enhancing film having a 75 micron thickness). The polymerizable composition is preferably sufficiently crosslinked to provide a glass transition temperature that is typically greater than 45° C. The glass transition temperature can be measured by methods known in the art, such as Differential Scanning calorimetry (DSC), modulated DSC, or Dynamic Mechanical Analysis. The polymerizable composition can be polymerized by conventional free radical polymerization methods.

The presently described optical films are prepared from a polymerizable resin composition comprising at least one triphenyl monomer comprising polymerizable ethylenically unsaturated substituents. The ethylenically unsaturated substituents are preferably (meth)acrylate substituents.

Such monomers comprise a triphenyl core structure wherein the three phenyl groups are not fused, but joined by a bond. At least one of the phenyl groups has a substituent comprising a polymerizable (meth)acrylate or thio(meth)acrylate (e.g. end) group. In some embodiments, the triphenyl monomer is a monofunctional (meth)acrylate monomer. Such monofunctional triphenyl monomer is preferably employed in combination with other multi- and in particular di-(meth)acrylate monomers. In other embodiments, the triphenyl monomer is a multi-(meth)acrylate monomer wherein two or more of the aromatic rings of the triphenyl core structure comprise (meth)acrylate or thio(meth)acrylate substituents.

In one embodiment, the triphenyl monomer has the general structure

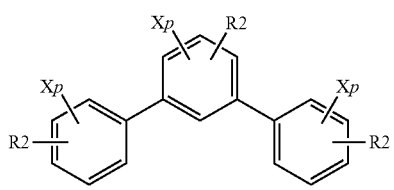

(T-1)

In another embodiment, the triphenyl monomer has the general structure

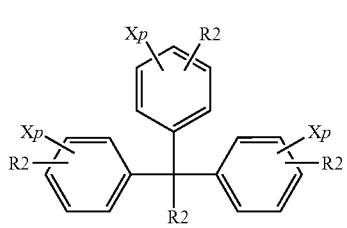

(T-2)

In yet another embodiment, the triphenyl monomer has the general structure

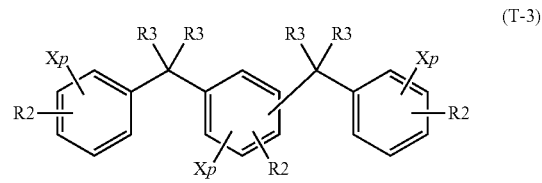

(T-3)

In each of the structures T-1, T-2, and T-3, R2 is independently H, methyl, or a substituent comprising a (meth)acrylate group and at least one R2 comprises a (meth)acrylate group; X is independently halogen, aryl, or a $C_2$ to $C_{12}$ alkyl group; and p is 0 to 5. R3 is independently hydrogen, methyl, aryl, or a $C_2$ to $C_{12}$ alkyl group. The alkyl group of X or R3 may have a straight chain or may be branched.

The triphenyl monomer is preferably free of bromine and chlorine-containing substituents. In some embodiments, the triphenyl monomer is substantially free of other halogen-containing substituents as well.

In some embodiments, p is 0 and thus the aromatic rings of the triphenyl core structure are unsubstituted, i.e. do not include any halogen or alkyl substituents.

R2 is independently H, methyl, or a substituent comprising a (meth)acrylate group and at least one R2 comprises a (meth)acrylate group. R2 is typically independently a (meth)acrylate substituent selected from i)

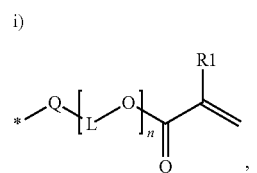

ii)

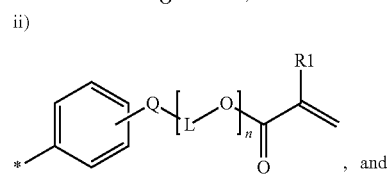

, and iii)

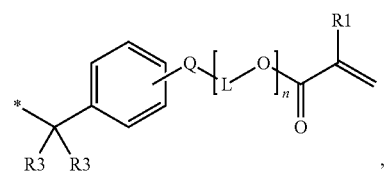

, wherein Q is O or S;
L is a $C_2$ to $C_6$ alkylene group optionally substituted with a one or more hydroxyl groups;
n ranges from 0 to 10;
R1 is H or $CH_3$; and
R3 is independently hydrogen, methyl, aryl, or a $C_1$ to $C_{12}$ alkyl group as previously described.

Based on starting materials that are known to be commercially available, R2 is typically i) or ii) for the triphenyl monomer of structure T-1. Further, for the triphenyl monomer of the structure T-3, R2 is typically i) or iii).

In some embodiments, Q is preferably O. L is preferably $C_2$ or $C_3$. Further, n is preferably 0, 1, or 2 and in some embodiments preferably 1.

The triphenyl (meth)acrylate monomers described herein can be prepared by synthetic methods as known by one of ordinary skill in the art. For example, triphenyl (meth)acrylate monomers can be prepared by the reaction of a triphenyl alcohol-group containing material with a (meth)acrylic acid or ester compound. In yet another synthesis, a triphenyl alcohol-group containing material can be reacted with an aromatic acid (e.g. para-toluene sulfonic acid) and a (meth) acrylic acid or ester compound. Alternatively, an epoxy starting material can be reacted with a (meth)acrylic acid or ester compound in the presence of a catalyst.

In some embodiments, the starting aromatic monoalcohol, diol, or triol is commercially available. In other embodiments, the starting aromatic alcohols can be synthesized.

Exemplary synthesis of acrylic acid 2-(4-{1,1-bis-[4-(2-acryloyloxy-ethoxy)-phenyl]-ethyl}-phenoxy)-ethyl ester ("TTA-1") and 2,6-diphenylphenoxyehyl acrylate ("TPA-1") are described in the forthcoming examples.

Other non-limiting examples of starting materials that can be used include:

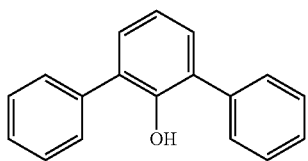

(S-1)

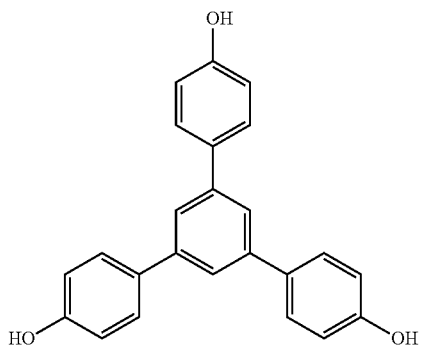

(S-2)

Various starting materials having the following general structure are known having the R5, R6, R7 and R8 group as specified in Table 1 as follows:

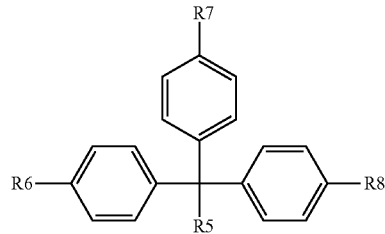

TABLE 1

| | R5 | R6 | R7 | R8 |
|---|---|---|---|---|
| S-3 | *—OH | *—H | *—H | *—H |
| S-4 | *—O⟨epoxy⟩ | *—H | *—H | *—H |
| S-5 | *—H | *—OH | *—OH | *—OH |
| S-6 | *—CH$_3$ | *—OH | *—H | *—OH |
| S-7 | *—CH$_3$ | *—OH | *—OH | *—OH |
| S-8 | *—⟨C$_6$H$_4$-OH⟩ | *—H | *—H | *—H |
| S-9 | *—⟨C$_6$H$_4$-OH⟩ | *—H | *—OH | *—H |
| S-10 | *—CH$_3$ | *—OH | *—OH | *—C(CH$_3$)$_2$-C$_6$H$_4$-OH |

Various starting materials having the following general structure are known having the R9-R15 groups as specified in Table 2 as follows:

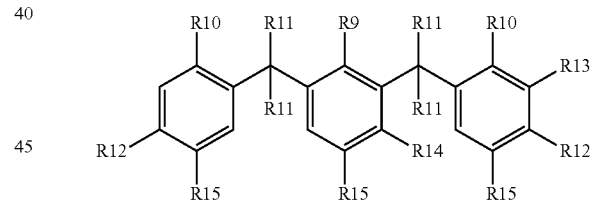

TABLE 2

| | R9 | R10 | R11 | R12 | R13 | R14 | R15 |
|---|---|---|---|---|---|---|---|
| S-11 | *—OH | *—OH | *—H | *—H | *—H | *—H | *—CH$_3$ |
| S-12 | *—H | *—H | *—CH$_3$ | *—H | *—H | *—OH | *—H |
| S-13 | *—H | *—H | *—CH$_3$ | *—OH | *—H | *—H | *—H |
| S-14 | *—OH | *—H | *—H | *—H | *—H | *—H | *—H |
| S-15 | *—OH | *—OH | *—H | *—H | ⟨CH$_2$-C$_6$H$_3$(OH)(CH$_3$)⟩ | *—H | *—CH$_3$ |

Another starting material is:

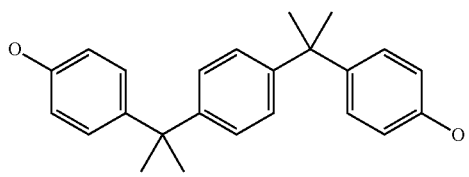

These starting materials are commercially available from various suppliers including Aldrich, TCI, and VWR.

After reaction, the polymerizable —OH or =O group(s) of each of the starting material are reacted to synthesize a molecule containing a (meth)acrylate containing substituent such as i), ii), or iii) as described above.

Preferred species of triphenyl monomers include multi-(meth)acrylates triphenyl monomers such as triphenyl tri(meth)acrylate monomers having a refractive index of at least 1.50, triphenyl di(meth)acrylate monomer having a refractive index of at least 1.55 and triphenyl mono(meth)acrylate monomers having a refractive index of at least 1.55. Triphenyl monomers that are a (e.g. viscous) liquid at ambient temperature (i.e. 25° C.) are also preferred for processing.

One preferred triphenyl monomer has the general structure

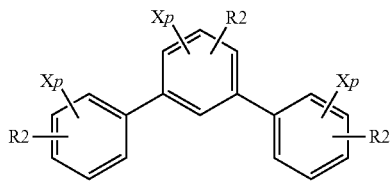

wherein X is independently halogen, aryl, or a $C_2$ to $C_{12}$ alkyl group;
p is 0 to 5; and
R2 is independently H or a substituent comprising a (meth)acrylate group and at least one
R2 comprises a substituent comprising a (meth)acrylate group selected from i)

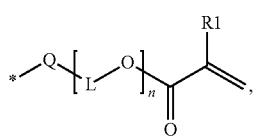

ii)

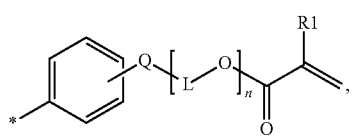

and
wherein Q is O or S;
L is a $C_2$ to $C_6$ alkylene group optionally substituted with a one or more hydroxyl groups;
n ranges from 1 to 10; and
R1 is H or $CH_3$.

The amount of triphenyl (meth)acrylate monomer employed in the polymerizable resin composition can vary. In some embodiments, the polymerizable compositions may consist solely (i.e. 100%) of a single multi-(meth)acrylate triphenyl monomer such as a di(meth)acrylate triphenyl monomer or a tri(meth)acrylate triphenyl monomer. In other embodiments, the polymerizable composition may comprise a mixture of two or more triphenyl monomers wherein at least one of the triphenyl (meth)acrylate monomers is a multi-(meth)acrylate. A small concentration, for example 1 wt-%, 2 wt-%, 3 wt-%, 4 wt-%, or 5 wt-% may be substituted for a portion of a lower refractive index component(s) in order to raise the refractive index of the polymerizable resin composition.

In yet other embodiments, the polymerizable resin comprises up to 50 wt-% of one or more triphenyl (meth)acrylate monomers; and 25 wt-% to 75 wt-% of one or more di(meth)acrylate monomers or oligomers having at least two polymerizable (meth)acrylate groups.

A variety of monomers and/or oligomers having at least two polymerizable (meth)acrylate groups may be employed.

Suitable urethane (meth)acrylates are commercially available from Sartomer under the trade designations "CN965", "CN968", "CN981", "CN 983", "CN 984", "CN972", and "CN978"; from Cognis under the trade designation "Photomer 6210", "Photomer 6217", "Photomer 6230", "Photomer 6623", "Photomer 6891", and "Photomer 6892"; and from UCB under the trade designations "Ebecryl 1290", "Ebecryl 2001", and "Ebecryl 4842".

Suitable polyester (meth)acrylates and (meth)acrylated acrylic oligomers are also commercially available or can be prepared by methods know in the art.

In some embodiments, the aromatic monomer is a bisphenol di(meth)acrylate, i.e. the reaction product of a bisphenol A diglycidyl ether and acrylic acid. Although bisphenol A diglycidyl ether is generally more widely available, it is appreciated that other biphenol diglycidyl ether such as bisphenol F diglycidyl ether could also be employed. In other embodiments, the monomer is an aromatic epoxy di(meth)acrylate oligomer derived from a different starting monomer.

Regardless of the starting monomers, the polymerizable composition preferably comprises at least one aromatic (optionally brominated) difunctional (meth)acrylate monomer that comprises a major portion having the following general structure:

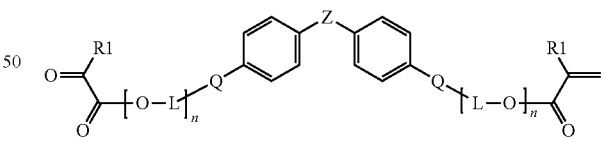

wherein Z is independently —$C(CH_3)_2$—, —$CH_2$—, —C(O)—, —S—, —S(O)—, or —$S(O)_2$—, each Q is independently O or S. L is a linking group. L may independently comprise a branched or linear $C_2$-$C_6$ alkylene group and n ranges from 0 to 10. More preferably L is $C_2$ or $C_3$ and n is 0, 1, 2 or 3. The carbon chain of the alkylene linking group may optionally be substituted with one or more hydroxy groups. For example L may be —$CH_2$CH(OH)$CH_2$—. Typically, the linking groups are the same. R1 is independently hydrogen or methyl.

The di(meth)acrylate monomer may be synthesized or purchased. As used herein, major portion refers to at least 60-70 wt-% of the monomer containing the specific structure(s) just described. It is commonly appreciated that other reaction products are also typically present as a byproduct of the synthesis of such monomers. The di(meth)acrylate monomer can be the reaction product of Tetrabromobisphenol A diglycidyl ether and acrylic acid. Such monomer may be obtained from UCB Corporation, Smyrna, Ga. under the trade designation "RDX-51027". This material comprises a major portion of 2-propenoic acid, (1-methylethylidene)bis[(2,6-dibromo-4,1-phenylene)oxy(2-hydroxy-3,1-propanediyl)] ester.

Alternatively or in addition to, the organic component may comprise one or more (meth)acrylated aromatic epoxy oligomers. Various (meth)acrylated aromatic epoxy oligomers are commercially available. For example, (meth)acrylated aromatic epoxy, (described as a modified epoxy acrylates), are available from Sartomer, Exton, Pa. under the trade designation "CN118", and "CN115". (Meth)acrylated aromatic epoxy oligomer, (described as an epoxy acrylate oligomer), is available from Sartomer under the trade designation "CN2204". Further, a (meth)acrylated aromatic epoxy oligomer, (described as an epoxy novolak acrylate blended with 40% trimethylolpropane triacrylate), is available from Sartomer under the trade designation "CN112C60". One exemplary aromatic epoxy acrylate is commercially available from Sartomer under the trade designation "CN 120" (reported by the supplier to have a refractive index of 1.5556, a viscosity of 2150 at 65° C., and a Tg of 60° C.).

In some embodiments, the aromatic epoxy acrylate is derived from bisphenol A, such as those of the structure previously described. In other embodiments, the aromatic epoxy acrylate is derived from a different monomer than bisphenol A.

One exemplary bisphenol-A ethoxylated diacrylate monomer is commercially available from Sartomer under the trade designations "SR602" (reported to have a viscosity of 610 cps at 20° C. and a Tg of 2° C.). Another exemplary bisphenol-A ethoxylated diacrylate monomer is as commercially available from Sartomer under the trade designation "SR601" (reported to have a viscosity of 1080 cps at 20° C. and a Tg of 60° C.).

In yet another embodiment, one or more of the triphenyl (meth)acrylate monomer(s) described here can be combined with one or more biphenyl (meth)acrylate monomers.

In some embodiments, the biphenyl (meth)acrylate monomer has the general structure

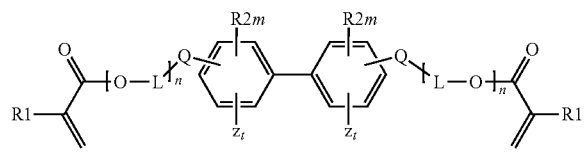

(B-1)

wherein each R1 is independently H or methyl;
each R2 is independently Br;
m ranges from 0 to 4;
each Q is independently O or S;
n ranges from 0 to 10;
L is a C2 to C12 alkylene group optionally substituted with one or more hydroxyl groups;
z is an aromatic ring; and
t is independently 0 or 1.

In some aspects, Q is preferably 0. Further, n is typically 0, 1 or 2. L is typically $C_2$ or $C_3$. Alternatively, L is typically a hydroxyl substituted $C_2$ or $C_3$. In some embodiments, z is preferably fused to the phenyl group thereby forming a binapthyl core structure.

Preferably, at least one of the -Q[L-O]n C(O)C(R1)=CH$_2$ groups is substituted at the ortho or meta position. More preferably, the biphenyl di(meth)acrylate monomer comprises a sufficient amount of ortho and/or meta (meth)acrylate substituents such that the monomer is a liquid at 25° C. In some embodiments, each (meth)acrylate group containing substituent is bonded to an aromatic ring group at an ortho or meta position. It is preferred that the biphenyl di(meth)acrylate monomer comprises a major amount of ortho (meth) acrylate substituents (i.e. at least 50%, 60%, 70%, 80%, 90%, or 95% of the substituents of the biphenyl di(meth)acrylate monomer). In some embodiments, each (meth)acrylate group containing substituent is bonded to an aromatic ring group at an ortho or meta position. As the number of meta- and particularly para-substituents increases, the viscosity of the organic components can increase as well. Further, para-biphenyl di(meth)acrylate monomers are solids at room temperature, with little solubility (i.e. less than 10%), even in phenoxyethyl acrylate and tetrahydrofurfuryl acrylate.

Such biphenyl monomers are described in further detail in WO2008/112451. Other biphenyl di(meth)acrylate monomer are described in the literature.

In other embodiments, the triphenyl (meth)acrylate containing polymerizable resin compositions optionally comprises one or more monofunctional diluents in amounts up to about 50 wt-%. In some embodiments, the polymerizable resin composition comprises at least 5 wt-%, 10 wt-% or 15 wt-% of such monofunctional diluents to improve the processability of the resin composition by reducing its viscosity.

Aromatic (e.g. monofunctional) (meth)acrylate monomers typically comprise a phenyl, cumyl, biphenyl, or naphthyl group. Preferred diluents can have a refractive index greater than 1.50 (e.g. greater than 1.55. Such reactive diluents can be halogenated, non-brominated, or non-halogenated.

Suitable monomers include phenoxyethyl (meth)acrylate; phenoxy-2-methylethyl (meth)acrylate; phenoxyethoxyethyl (meth)acrylate, 3-hydroxy-2-hydroxypropyl (meth)acrylate; benzyl (meth)acrylate; phenylthio ethyl acrylate; 2-naphthylthio ethyl acrylate; 1-naphthylthio ethyl acrylate; naphthyloxy ethyl acrylate; 2-naphthyloxy ethyl acrylate; phenoxy 2-methylethyl acrylate; phenoxyethoxyethyl acrylate; 3-phenoxy-2-hydroxy propyl acrylate; and phenyl acrylate.

Phenoxyethyl acrylate is commercially available from more than one source including from Sartomer under the trade designation "SR339"; from Eternal Chemical Co. Ltd. under the trade designation "Etermer 210"; and from Toagosei Co. Ltd under the trade designation "TO-1166". Phenylthio ethyl acrylate (PTEA) is also commercially available from Cognis. The structure of these monomers is shown as follows:

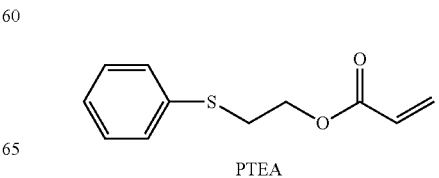

PTEA

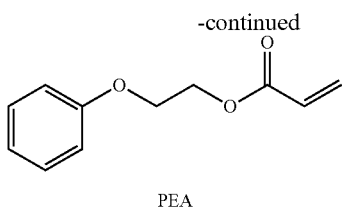

PEA

In some embodiments, the polymerizable compositions comprise one or more monofunctional biphenyl monomer(s).

Monofunctional biphenyl monomers comprise a terminal biphenyl group (wherein the two phenyl groups are not fused, but joined by a bond) or a terminal group comprising two aromatic groups joined by a linking group (e.g. Q). For example, when the linking group is methane, the terminal group is a biphenylmethane group. Alternatively, wherein the linking group is —C(CH$_3$)$_2$—, the terminal group is 4-cumyl phenyl. The monofunctional biphenyl monomer(s) also comprise a single ethylenically unsaturated group that is preferably polymerizable by exposure to (e.g. UV) radiation. The monofunctional biphenyl monomer(s) preferably comprise a single (meth)acrylate group or single thio(meth)acrylate group. Acrylate functionality is typically preferred. In some aspects, the biphenyl group is joined directly to the ethylenically unsaturated (e.g. (meth)acrylate) group. An exemplary monomer of this type is 2-phenyl-phenyl acrylate. The biphenyl mono(meth)acrylate or biphenyl thio(meth)acrylate monomer may further comprise a (e.g. 1 to 5 carbon) alkyl group optionally substituted with one or more hydroxyl groups. An exemplary species of this type is 2-phenyl-2-phenoxyethyl acrylate.

In one embodiment, a monofunctional biphenyl (meth) acrylate monomer is employed having the general formula:

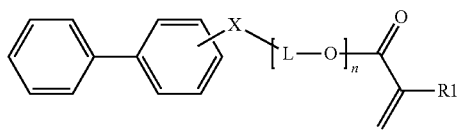

wherein R1 is H or CH$_3$;

X is O or S;

n ranges from 0 to 10 (e.g. n is 1, 2, 3, 4, 5, 6, 7, 8, 9, or 10); and

L is an alkylene group having 1 to 5 carbon atoms (i.e. methylene, ethylene, propylene, butylene, or pentylene), optionally substituted with hydroxy.

In another embodiment, the monofunctional biphenyl (meth)acrylate monomer has the general formula:

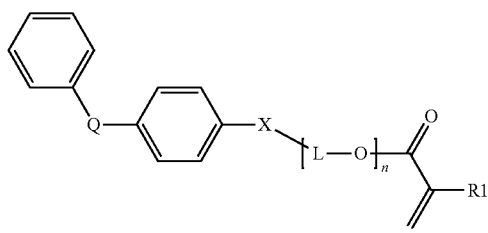

wherein R1 is H or CH$_3$;

X is O or S;

Q is selected from —C(CH$_3$)$_2$—, —CH$_2$, —C(O)—, —S(O)—, and —S(O)$_2$—;

n ranges from 0 to 10 (e.g. n is 1, 2, 3, 4, 5, 6, 7, 8, 9, or 10); and

L is an alkylene group having 1 to 5 carbon atoms (i.e. methylene, ethylene, butylene, or pentylene), optionally substituted with hydroxy.

Some specific monomers that are commercially available from Toagosei Co. Ltd. of Japan, include for example 2-phenyl-phenyl acrylate available under the trade designation "TO-2344", 4-(-2-phenyl-2-propyl)phenyl acrylate available under the trade designation "TO-2345", and 2-phenyl-2-phenoxyethyl acrylate, available under the trade designation "TO-1463".

Various combinations of aromatic monofunctional (meth) acrylate monomers can be employed. For example, a (meth) acrylate monomer comprising a phenyl group may be employed in combination with one or more (meth)acrylate monomers comprising a biphenyl group. Further, two different biphenyl (meth)acrylate monofunctional monomera may be employed.

The polymerizable resin may optionally comprise up to 35 wt-% of various other (e.g. non-halogenated) ethylenically unsaturated monomers. For example, when the (e.g. prism) structures are cast and photocured upon a polycarbonate preformed polymeric film the polymerizable resin composition may comprise one or more N,N-disubstituted (meth)acrylamide monomers. These include N-alkylacrylamides and N,N-dialkylacrylamides, especially those containing C$_{1-4}$ alkyl groups. Examples are N-isopropylacrylamide, N-t-butylacrylamide, N,N-dimethylacrylamide, N,N-diethylacrylamide, N-vinyl pyrrolidone and N-vinylcaprolactam.

The polymerizable resin composition may also optionally comprise up to 20 wt-% of a non-aromatic crosslinker that comprises at least three (meth)acrylate groups. Suitable crosslinking agents include for example pentaerythritol tri(meth)acrylate, pentaerythritol tetra(meth)acrylate, trimethylolpropane tri(methacrylate), dipentaerythritol penta(meth) acrylate, dipentaerythritol hexa(meth)acrylate, trimethylolpropane ethoxylate tri(meth)acrylate, glyceryl tri(meth)acrylate, pentaerythritol propoxylate tri(meth)acrylate, and ditrimethylolpropane tetra(meth)acrylate. Any one or combination of crosslinking agents may be employed. Since methacrylate groups tend to be less reactive than acrylate groups, the crosslinker(s) are preferably free of methacrylate functionality.

Various crosslinkers are commercially available. For example, pentaerythritol triacrylate (PETA) is commercially available from Sartomer Company, Exton, Pa. under the trade designation "SR444"; from Osaka Organic Chemical Industry, Ltd. Osaka, Japan under the trade designation "Viscoat #300"; from Toagosei Co. Ltd., Tokyo, Japan under the trade designation "Aronix M-305"; and from Eternal Chemical Co., Ltd., Kaohsiung, Taiwan under the trade designation "Etermer 235". Trimethylol propane triacrylate (TMPTA) is commercially available from Sartomer Company under the trade designations "SR351". TMPTA is also available from Toagosei Co. Ltd. under the trade designation "Aronix M-309". Further, ethoxylated trimethylolpropane triacrylate and ethoxylated pentaerythritol triacrylate are commercially available from Sartomer under the trade designations "SR454" and "SR494" respectively.

In some embodiments, it is preferred that the polymerized microstructured surface of the optical film, the polymerizable resin composition, and the triphenyl monomers are substantially free (i.e. contain less than 1 wt-%) of bromine. In other embodiments, the total amount of bromine in combination with chlorine is less than 1 wt-%. In some aspects, the polymerized microstructured surface or the optical film, the polymerizable resin composition, and the triphenyl monomers are substantially non-halogenated (i.e. contains less than 1 wt-% total of bromine, chlorine, fluorine and iodine).

The UV curable polymerizable compositions comprise at least one photoinitiator. A single photoinitiator or blends thereof may be employed in the brightness enhancement film of the invention. In general the photoinitiator(s) are at least partially soluble (e.g. at the processing temperature of the resin) and substantially colorless after being polymerized. The photoinitiator may be (e.g. yellow) colored, provided that the photoinitiator is rendered substantially colorless after exposure to the UV light source.

Suitable photoinitiators include monoacylphosphine oxide and bisacylphosphine oxide. Commercially available mono or bisacylphosphine oxide photoinitiators include 2,4,6-trimethylbenzoybiphenylphosphine oxide, commercially available from BASF (Charlotte, N.C.) under the trade designation "Lucirin TPO"; ethyl-2,4,6-trimethylbenzoylphenyl phosphinate, also commercially available from BASF under the trade designation "Lucirin TPO-L"; and bis(2,4,6-trimethylbenzoyl)-phenylphosphine oxide commercially available from Ciba Specialty Chemicals under the trade designation "Irgacure 819". Other suitable photoinitiators include 2-hydroxy-2-methyl-1-phenyl-propan-1-one, commercially available from Ciba Specialty Chemicals under the trade designation "Darocur 1173" as well as other photoinitiators commercially available from Ciba Specialty Chemicals under the trade designations "Darocur 4265", "Irgacure 651", "Irgacure 1800", "Irgacure 369", "Irgacure 1700", and "Irgacure 907".

The photoinitiator can be used at a concentration of about 0.1 to about 10 weight percent. More preferably, the photoinitiator is used at a concentration of about 0.5 to about 5 wt-%. Greater than 5 wt-% is generally disadvantageous in view of the tendency to cause yellow discoloration of the brightness enhancing film. Other photoinitiators and photoinitiator may also suitably be employed as may be determined by one of ordinary skill in the art.

Surfactants such as fluorosurfactants and silicone based surfactants can optionally be included in the polymerizable composition to reduce surface tension, improve wetting, allow smoother coating and fewer defects of the coating, etc.

The triphenyl (meth)acrylate monomers described herein are particularly useful in preparing non-halogenated high refractive index polymerizable organic compositions. In some aspects the compositions are free of inorganic nanoparticles.

In other embodiments, the polymerizable composition further comprises inorganic nanoparticles.

Surface modified (e.g. colloidal) nanoparticles can be present in the polymerized structure in an amount effective to enhance the durability and/or refractive index of the article or optical element. In some embodiments, the total amount of surface modified inorganic nanoparticles can be present in the polymerizable resin or optical article in an amount of at least 10 wt-%, 20 wt-%, 30 wt-% or 40 wt-%. The concentration is typically less than to 70 wt-%, and more typically less than 60 wt-% in order that the polymerizable resin composition has a suitable viscosity for use in cast and cure processes of making microstructured films.

The size of such particles is chosen to avoid significant visible light scattering. It may be desirable to employ a mixture of inorganic oxide particle types to optimize an optical or material property and to lower total composition cost. The surface modified colloidal nanoparticles can be oxide particles having a (e.g. unassociated) primary particle size or associated particle size of greater than 1 nm, 5 nm or 10 nm. The primary or associated particle size is generally and less than 100 nm, 75 nm, or 50 nm. Typically the primary or associated particle size is less than 40 nm, 30 nm, or 20 nm. It is preferred that the nanoparticles are unassociated. Their measurements can be based on transmission electron microscopy (TEM). The nanoparticles can include metal oxides such as, for example, alumina, zirconia, titania, mixtures thereof, or mixed oxides thereof. Surface modified colloidal nanoparticles can be substantially fully condensed.

Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

Zirconia and titania nanoparticles can have a particle size from 5 to 50 nm, or 5 to 15 nm, or 8 nm to 12 nm. Zirconia nanoparticles can be present in the durable article or optical element in an amount from 10 to 70 wt-%, or 30 to 60 wt-%. Zirconias for use in composition and articles of the invention are available from Nalco Chemical Co. under the trade designation "Nalco OOSSOO8" and from Buhler AG Uzwil, Switzerland under the trade designation "Buhler zirconia Z-WO sol".

The zirconia particles can be prepared using hydrothermal technology as described in Published U.S. Patent Application No. 2006/0148950. The nanoparticles are surface modified. Surface modification involves attaching surface modification agents to inorganic oxide (e.g. zirconia) particles to modify the surface characteristics. The overall objective of the surface modification of the inorganic particles is to provide resins with homogeneous components and preferably a low viscosity that can be prepared into films (e.g. using cast and cure processes) with high brightness.

The nanoparticles are often surface-modified to improve compatibility with the organic matrix material. The surface-modified nanoparticles are often non-associated, non-agglomerated, or a combination thereof in an organic matrix material. The resulting light management films that contain these surface-modified nanoparticles tend to have high optical clarity and low haze. The addition of the high refractive index surface-modified nanoparticles, such as zirconia, can increase the gain of brightness enhancement film compared to films that contain only polymerized organic material.

The monocarboxylic acid surface treatments preferably comprise a compatibilizing group. The monocarboxylic acids may be represented by the formula A-B where the A group is a (e.g. monocarboxylic acid) group capable of attaching to the surface of a (e.g. zirconia or titania) nanoparticle, and B is a compatibilizing group that comprises a variety of different functionalities. The carboxylic acid group can be attached to the surface by adsorption and/or formation of an ionic bond. The compatibilizing group B is generally chosen such that it is compatible with the polymerizable resin of the (e.g. brightness enhancing) optical article. The compatibilizing group B can be reactive or nonreactive and can be polar or non-polar.

Compatibilizing groups B that can impart non-polar character to the zirconia particles include, for example, linear or branched aromatic or aliphatic hydrocarbons. Representative examples of non-polar modifying agents having carboxylic acid functionality include octanoic acid, dodecanoic acid, stearic acid, oleic acid, and combinations thereof The compatibilizing group B may optionally be reactive such that it can copolymerize with the organic matrix of the (e.g. brightness enhancing) optical article. For instance, free radically polymerizable groups such as (meth)acrylate compatibilizing groups can copolymerize with (meth)acrylate functional organic monomers to generate brightness enhancement articles with good homogeneity.

Suitable surface modifications are described in U.S. Publication No. 2007/0112097 and U.S. Serial No. WO2008/121465.

The surface modified particles can be incorporated into the curable (i.e. polymerizable) resin compositions in various methods. In a preferred aspect, a solvent exchange procedure is utilized whereby the resin is added to the surface modified sol, followed by removal of the water and co-solvent (if used) via evaporation, thus leaving the particles dispersed in the polymerizable resin. The evaporation step can be accomplished for example, via distillation, rotary evaporation or oven drying. In another aspect, the surface modified particles can be extracted into a water immiscible solvent followed by solvent exchange, if so desired. Alternatively, another method for incorporating the surface modified nanoparticles in the polymerizable resin involves the drying of the modified particles into a powder, followed by the addition of the resin material into which the particles are dispersed. The drying step in this method can be accomplished by conventional means suitable for the system, such as, for example, oven drying or spray drying.

The optical layer can directly contact the base layer or be optically aligned to the base layer, and can be of a size, shape and thickness allowing the optical layer to direct or concentrate the flow of light. The optical layer can have a structured or micro-structured surface that can have any of a number of useful patterns such as described and shown in the U.S. Pat. No. 7,074,463. The micro-structured surface can be a plurality of parallel longitudinal ridges extending along a length or width of the film. These ridges can be formed from a plurality of prism apexes. These apexes can be sharp, rounded or flattened or truncated. For example, the ridges can be rounded to a radius in a range of 4 to 7 to 15 micrometers.

These include regular or irregular prismatic patterns, which can be an annular prismatic pattern, a cube-corner pattern or any other lenticular microstructure. A useful microstructure is a regular prismatic pattern that can act as a totally internal reflecting film for use as a brightness enhancement film. Another useful microstructure is a corner-cube prismatic pattern that can act as a retro-reflecting film or element for use as reflecting film. Another useful microstructure is a prismatic pattern that can act as an optical element for use in an optical display. Another useful microstructure is a prismatic pattern that can act as an optical turning film or element for use in an optical display.

The base layer can be of a nature and composition suitable for use in an optical product, i.e. a product designed to control the flow of light. Almost any material can be used as a base material as long as the material is sufficiently optically clear and is structurally strong enough to be assembled into or used within a particular optical product. A base material can be chosen that has sufficient resistance to temperature and aging that performance of the optical product is not compromised over time.

Useful base materials include, for example, styrene-acrylonitrile, cellulose acetate butyrate, cellulose acetate propionate, cellulose triacetate, polyether sulfone, polymethyl methacrylate, polyurethane, polyester, polycarbonate, polyvinyl chloride, polystyrene, polyethylene naphthalate, copolymers or blends based on naphthalene dicarboxylic acids, polycyclo-olefins, polyimides, and glass. Optionally, the base material can contain mixtures or combinations of these materials. In an embodiment, the base may be multi-layered or may contain a dispersed component suspended or dispersed in a continuous phase.

For some optical products such as microstructure-bearing products such as, for example, brightness enhancement films, examples of preferred base materials include polyethylene terephthalate (PET) and polycarbonate. Examples of useful PET films include photograde polyethylene terephthalate and MELINEX™ PET available from DuPont Films of Wilmington, Del.

Some base materials can be optically active, and can act as polarizing materials. A number of bases, also referred to herein as films or substrates, are known in the optical product art to be useful as polarizing materials. Polarization of light through a film can be accomplished, for example, by the inclusion of dichroic polarizers in a film material that selectively absorbs passing light. Light polarization can also be achieved by including inorganic materials such as aligned mica chips or by a discontinuous phase dispersed within a continuous film, such as droplets of light modulating liquid crystals dispersed within a continuous film. As an alternative, a film can be prepared from microfine layers of different materials. The polarizing materials within the film can be aligned into a polarizing orientation, for example, by employing methods such as stretching the film, applying electric or magnetic fields, and coating techniques.

Examples of polarizing films include those described in U.S. Pat. Nos. 5,825,543 and 5,783,120. The use of these polarizer films in combination with a brightness enhancement film has been described in U.S. Pat. No. 6,111,696.

A second example of a polarizing film that can be used as a base are those films described in U.S. Pat. No. 5,882,774. Films available commercially are the multilayer films sold under the trade designation DBEF (Dual Brightness Enhancement Film) from 3M. The use of such multilayer polarizing optical film in a brightness enhancement film has been described in U.S. Pat. No. 5,828,488.

A common way of measuring the effectiveness of such recycling of light is to measure the gain of an optical film. As used herein, "relative gain", is defined as the on-axis luminance, as measured by the test method described in the examples, when an optical film (or optical film assembly) is placed on top of the light box, relative to the on-axis luminance measured when no optical film is present on top of the light box. This definition can be summarized by the following relationship:

Relative Gain=(Luminance measured with optical film)/(Luminance measured without optical film)

In one embodiment, an optical film comprising a light transmissive (e.g. cured) polymeric material having a microstructured surface is described. The optical film is a substantially non-polarizing film having a single sheet relative gain of at least 1.60. The relative single sheet gain is typically no greater than 2.05. Accordingly, the single sheet relative gain may also range from any values in the set of relative gain values including 1.65, 1.70, 1.75, 1.80, 1.85, and 1.90 or greater.

In other embodiments, the inventions relate to various assemblies that comprise or consist of two or more films.

Each assembly includes a first microstructured optical film proximate a second (e.g. microstructured or unstructured) optical film.

By proximate, it is meant sufficiently near. Proximate can include the first microstructured optical film being in contact with the second optical film such as by the films merely being stacked together or the films may be attached by various means. The films may be attached by mechanical means, chemical means, thermal means, or a combination thereof. Chemical means includes various pressure sensitive, solvent-based, and hot melt adhesives as well as two-part curable adhesive compositions that crosslink upon exposure to heat, moisture, or radiation. Thermal means includes for example a heated embossed roller, radio frequency (RF) welding, and ultrasonic welding. The optical films may be attached (e.g. continuously) across the entire plane of the films, at only select points, or at only the edges. Alternatively, the proximate optical films may be separated from each other with an air interface. The air interface may be created by increasing the thickness of either or both optical films at the periphery, such as by application of an adhesive. When the films are stacked rather than laminated together, the air interface between the optical films may be only a few microns.

In some embodiments, a first microstructured optical film is proximate a second microstructured optical film. In such assemblies, the microstructured surface of the bottom film is preferably disposed proximate the unstructured surface of the top film. For embodiments that employ prismatic microstructured films, the prisms of the films are generally aligned parallel in one principal direction, the prisms being separated by grooves. It is generally preferred to align the prisms (or grooves) of the second (e.g. bottom) microstructured optical film in a stack such that the prisms are substantially orthogonal to the prisms of the first (e.g. top) film. However, other alignments can also be employed. For example, the prisms of the second optical film may be positioned relative to the prisms of the second optical film such that the intersection of grooves or prisms form angles ranging from about 70° to about 120°.

In one embodied assembly, a first microstructured substantially non-polarizing optical film is proximate a second microstructured substantially non-polarizing optical film. The gain of this assembly is at least 2.50. The first optical film may be the same as or different than the second optical film. For example, the second film may have a different base layer composition, a different microstructured surface composition, and/or may have a different surface microstructure. The relative gain of this assembly is typically less than 3.32. Accordingly, the relative gain of such assembly may also range from any values in the set of relative gain values including 2.55, 2.60, 2.65, 2.70, 2.75, 2.80, 2.85, 2.90, 2.95, and 3.00 or greater.

For the following defined terms, these definitions shall be applied, unless a different definition is given in the claims or elsewhere in this specification.

The term "microstructure" is used herein as defined and explained in U.S. Pat. No. 4,576,850. Thus, it means the configuration of a surface that depicts or characterizes the predetermined desired utilitarian purpose or function of the article having the microstructure. Discontinuities such as projections and indentations in the surface of said article will deviate in profile from the average center line drawn through the microstructure such that the sum of the areas embraced by the surface profile above the center line is equal to the sum of the areas below the line, said line being essentially parallel to the nominal surface (bearing the microstructure) of the article. The heights of said deviations will typically be about +/−0.005 to +/−750 microns, as measured by an optical or electron microscope, through a representative characteristic length of the surface, e.g., 1-30 cm. Said average center line can be piano, concave, convex, aspheric or combinations thereof. Articles where said deviations are of low order, e.g., from +/−0.005+/−0.1 or, preferably, +/−0.05 microns, and said deviations are of infrequent or minimal occurrence, i.e., the surface is free of any significant discontinuities, are those where the microstructure-bearing surface is an essentially "flat" or "smooth" surface, such articles being useful, for example, as precision optical elements or elements with a precision optical interface, such as ophthalmic lenses. Articles where said deviations are of low order and of frequent occurrence include those having anti-reflective microstructure. Articles where said deviations are of high-order, e.g., from +/−0.1 to +/−750 microns, and attributable to microstructure comprising a plurality of utilitarian discontinuities which are the same or different and spaced apart or contiguous in a random or ordered manner, are articles such as retroreflective cube-corner sheeting, linear Fresnel lenses, video discs and brightness enhancing films. The microstructure-bearing surface can contain utilitarian discontinuities of both said low and high orders. The microstructure-bearing surface may contain extraneous or non-utilitarian discontinuities so long as the amounts or types thereof do not significantly interfere with or adversely affect the predetermined desired utilities of said articles.

"Index of refraction," or "refractive index," refers to the absolute refractive index of a material (e.g., a monomer) that is understood to be the ratio of the speed of electromagnetic radiation in free space to the speed of the radiation in that material. The refractive index can be measured using known methods and is generally measured using an Abbe refractometer or Bausch and Lomb Refractometer (CAT No. 33.46.10) in the visible light region (available commercially, for example, from Fisher Instruments of Pittsburgh, Pa.). It is generally appreciated that the measured index of refraction can vary to some extent depending on the instrument.

"(Meth)acrylate" refers to both acrylate and methacrylate compounds.

The term "nanoparticles" is defined herein to mean particles (primary particles or associated primary particles) with a diameter less than about 100 nm.

"Surface modified colloidal nanoparticle" refers to nanoparticles each with a modified surface such that the nanoparticles provide a stable dispersion.

"Stable dispersion" is defined herein as a dispersion in which the colloidal nanoparticles do not agglomerate after standing for a period of time, such as about 24 hours, under ambient conditions—e.g. room temperature (about 20-22° C.), atmospheric pressure, and no extreme electromagnetic forces.

"Aggregation" refers to a strong association between primary particles that may be chemically bound to one another. The breakdown of aggregates into smaller particles is difficult to achieve.

"Agglomeration" refers to a weak association between primary particles which may be held together by charge or polarity and can be broken down into smaller entities.

"Primary particle size" refers to the mean diameter of a single (non-aggregate, non-agglomerate) particle.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties and so forth used in the specification and claims are to be understood as being modified in all instances by the term "about."

The present invention should not be considered limited to the particular examples described herein, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

EXAMPLES

1. Synthesis of Acrylic acid 4-[1,1-bis-(4-acryloyloxy-phenyl)-ethyl]-phenyl ester A 500 ml round bottom flask is equipped with a mechanical stirrer, thermometer and addition funnel. Add 50 grams 1,1,1-tris(4-hydroxyphenyl) ethane, 180 grams DMF and 57.8 grams of triethylamine. Stir well at room temperature. Add 48.7 grams of acryloyl chloride dropwise to this mixture, keeping the pot temperature at 25-30° C. After completing the addition, stir the mixture for one hour at 25° C. Add 200 g. ethyl acetate and wash the organic portion four times with 150 g. water and then with 150 g. water/20 g. HCl, then with 150 g. saturated brine. Strip the solvent from the mix on a rotary evaporator.

Pass the crude mixture through a large silica gel column, using 20% ethyl acetate/80% hexanes as the elutant. Collect the appropriate product fractions and strip the solvent. Obtain 5 grams of an off-white solid. The mp is 130° C. and a refractive index of at least 1.55.

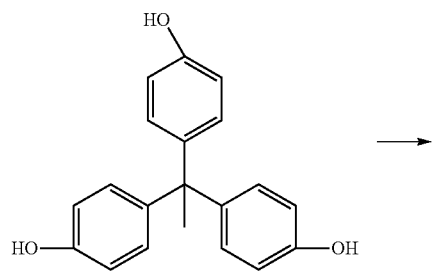

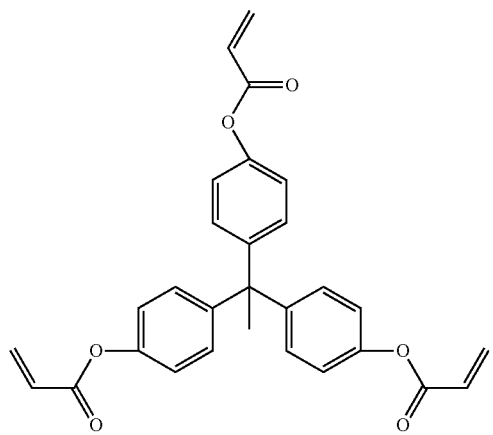

2. Synthesis of 2-(4-{1,1-bis-[4-(2-hydroxy-ethoxy)-phenyl]-ethyl}-phenoxy)-ethanol Intermediate A 500 ml round bottom flask is equipped with a mechanical stirrer, thermometer and condenser. Add 50 grams 1,1,1-tris(4-hydroxyphenyl) ethane, 100 grams DMF, 0.5 g. potassium iodide and 47.4 grams of ethylene carbonate. Heat to 145° C. and hold for 6 hours. Add 200 g. ethyl acetate and wash the organic portion four times with 150 g. saturated brine. Strip the solvent from the mix on a rotary evaporator. The yield of tan solid is 78 grams. Recrystallize this crude product by dissolving in 300 g. boiling ethyl acetate and allowing to cool slowly. Collect 70.3 grams of a tan solid; the mp=78-81° C.

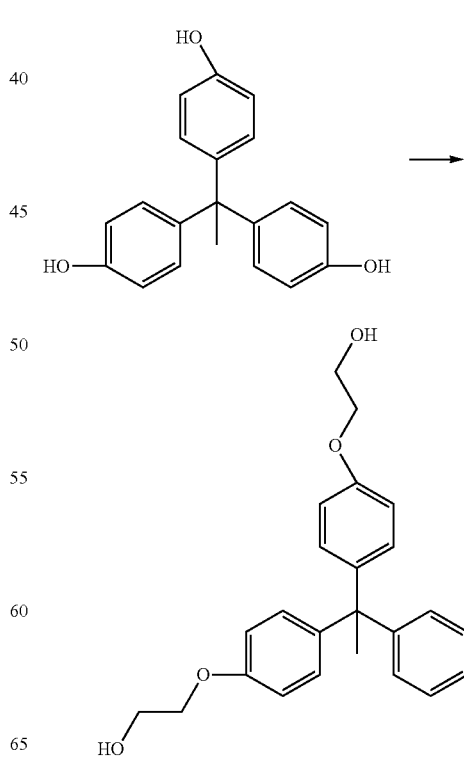

Synthesis of Acrylic acid 2-(4-{1,1-bis-[4-(2-acryloyloxy-ethoxy)-phenyl]-ethyl}-phenoxy)-ethyl ester ("TTA-1")

A 1000 ml round bottom flask is equipped with a mechanical stirrer, thermometer and dean-stark trap with condenser. Add 50 grams 2-(4-{1,1-Bis-[4-(2-hydroxy-ethoxy)-phenyl]-ethyl}-phenoxy)-ethanol, 400 grams toluene, 2 g. para-toluene sulfonic acid (PTSA), 27.1 grams acrylic acid and 0.04 grams of hindered amine nitroxide inhibitor commercially available from Ciba Specialty Chemical, Inc. Tarrytown, N.Y. under the trade designation "Prostab 5198". Heat to reflux and hold for 6 hours. Cool to room temperature, then add 0.7 grams PTSA and 7 grams acrylic acid. Heat to reflux and hold for five hours. Wash the organic portion with 250 g. water with 25 g sodium carbonate, then twice with 250 g. saturated brine. Strip the solvent from the mix on a rotary evaporator. The crude product is dissolved in 500 g ethyl acetate and passed through a short bed of silica gel with ethyl acetate as the elutant. Remove the solvent on a rotary evaporator to give 50 grams of a light yellow oil. The refractive index is 1.554.

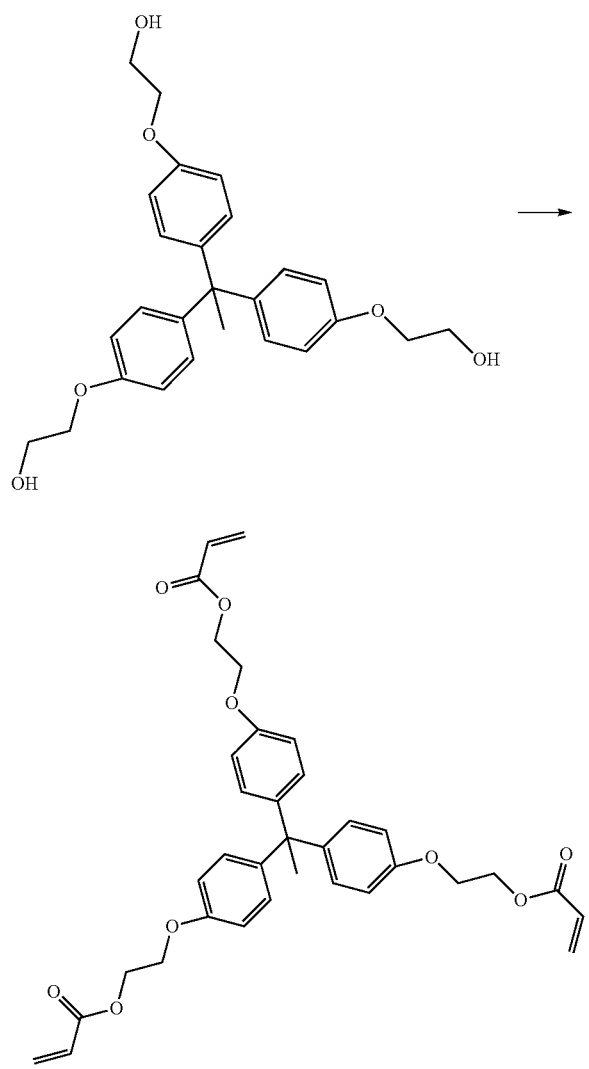

3. Synthesis of 2,6-Diphenylphenoxyethanol Intermediate

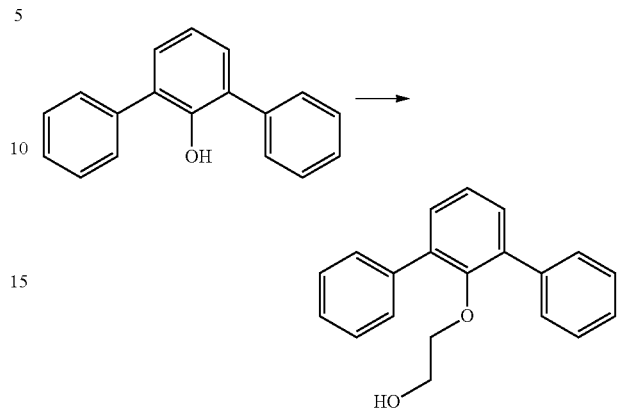

To a 50 ml 1 neck round bottom was added 2,6-diphenylphenol (10 g, 1 eq), ethylene carbonate (3.9 g, 1.1 eq), potassium iodide (0.07 g, 0.01 eq), dimethylformamide (1 g, 0.3 eq) and heated to 150 C. After 4 hours the reaction was cooled to 40 C, added 30 ml ethyl acetate and washed 2 times with 20 ml sodium chloride brine, 3 times with 20 ml DI water and again with 20 ml brine. The ethyl acetate was dried with (1 g) magnesium sulfate, filtered and concentrated invacuo to recover an off-white solid. Mp 77-78

Synthesis of 2,6-Diphenylphenoxyethyl acrylate ("TPA-1")

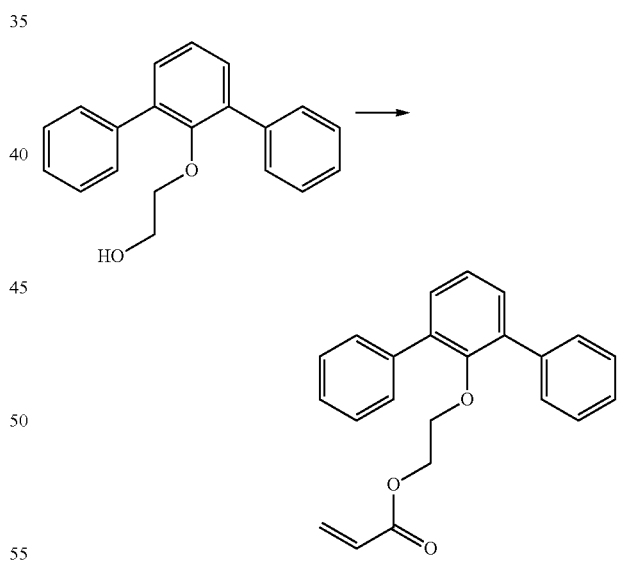

To a 50 ml 1 neck round bottom equipped with a dean stark trap was added 2,6-diphenylphenoxyethanol (5 g, 1 eq), toluene (21 ml), acrylic acid (2.7 g, 2.2 eq), methane sulfonic acid (0.3 g, 0.18 eq), Prostab 5198 (0.003 g) and heated to reflux. After 3 hours the reaction was complete. The reaction was washed with 20 ml sodium carbonate and 20 ml sodium chloride brine. The toluene mixture was filtered through thin layer of silica gel and eluted with 30 ml toluene. The filtrate was treated with the "Prostab 5198" (0.003 g) and concentrated invacuo to recover a viscous oil. >97% by GC. RI=1.6062 at 25° C.

Polymerizable Resin Composition 1: 65 parts CN120 (epoxy acrylate available from Sartomer Company, Exton, Pa., reported by Sartomer to have a viscosity of 2150 cps at 65° C., a refractive index of 1.5556 and a Tg of 60° C.), 15 parts SR339 (2-phenoxyethyl acrylate available from Sartomer Company, Exton, Pa., reported by Sartomer to have a viscosity of 12 cps at 25° C., a refractive index of 1.516 and a Tg of 5° C.), 20 parts TTA-1 (with a refractive index of 1.554), and 0.3 parts Darocur 4265 (available from Ciba Specialty Chemicals, Tarrytown, N.Y.) were mixed together thoroughly in an amber jar.

Polymerizable Resin Composition 2: 50 parts CN120, 50 parts TTA-1 (with a refractive index of 1.554), and 0.3 parts Darocur 4265 (available from Ciba Specialty Chemicals, Tarrytown, N.Y.) were mixed together thoroughly in an amber jar.

Polymerizable Resin Composition 3: 100 parts TTA-1 (with a refractive index of 1.554), and 0.3 parts Darocur 4265 (available from Ciba Specialty Chemicals, Tarrytown, N.Y.) were mixed together thoroughly in an amber jar.

Polymerizable Resin Composition 4: 30 parts of TPA-1 (with a refractive index of 1.606), 35 parts CN120, 35 parts SR601 (ethoxylated bisphenol A diacrylate available from Sartomer Company reported to have a viscosity of 1080 cps at 25° C., a refractive index of 1.5340 and a Tg of 60° C.) and 0.3 parts Darocur 4265 (available from Ciba Specialty Chemicals, Tarrytown, N.Y.) were mixed together thoroughly in an amber jar.

Optical Film Sample Preparation:

Brightness enhancing films samples were made using Polymerizable Resin Compositions 1 and 2. About 3 grams of warm resin was applied to a 2 mil primed PET (polyester) film, available from DuPont under the trade designation "Melinex 623" and placed against a microstructured tool with a 90/24 pattern similar to the commercially available Vikuiti TBEF-90/24. The PET, resin and tool were passed through a heated laminator set at approximately 150° F. to create a uniformly thick sample. The tool containing the film and coated resin sample was passed at 30 fpm through a Fusion UV processor containing two 600 W/in D-bulbs. The PET and cured resin were removed from the tool and cut into samples.

Gain Test Method

Optical performance of the films was measured using a SpectraScan™ PR-650 SpectraColorimeter with an MS-75 lens, available from Photo Research, Inc, Chatsworth, Calif. The films were placed on top of a diffusely transmissive hollow light box. The diffuse transmission and reflection of the light box can be described as Lambertian. The light box was a six-sided hollow cube measuring approximately 12.5 cm×12.5 cm×11.5 cm (L×W×H) made from diffuse PTFE plates of ~6 mm thickness. One face of the box is chosen as the sample surface. The hollow light box had a diffuse reflectance of ~0.83 measured at the sample surface (e.g. ~83%, averaged over the 400-700 nm wavelength range, measurement method described below). During the gain test, the box is illuminated from within through a ~1 cm circular hole in the bottom of the box (opposite the sample surface, with the light directed towards the sample surface from the inside). This illumination is provided using a stabilized broadband incandescent light source attached to a fiber-optic bundle used to direct the light (Fostec DCR-II with ~1 cm diameter fiber bundle extension from Schott-Fostec LLC, Marlborough Mass. and Auburn, N.Y.). A standard linear absorbing polarizer (such as Melles Griot 03 FPG 007) is placed between the sample box and the camera. The camera is focused on the sample surface of the light box at a distance of ~34 cm and the absorbing polarizer is placed ~2.5 cm from the camera lens. The luminance of the illuminated light box, measured with the polarizer in place and no sample films, was >150 cd/m². The sample luminance is measured with the PR-650 at normal incidence to the plane of the box sample surface when the sample films are placed parallel to the box sample surface, the sample films being in general contact with the box. The relative gain is calculated by comparing this sample luminance to the luminance measured in the same manner from the light box alone. The entire measurement was carried out in a black enclosure to eliminate stray light sources.

The diffuse reflectance of the light box was measured using a 15.25 cm (6 inch) diameter Spectralon-coated integrating sphere, a stabilized broadband halogen light source, and a power supply for the light source all supplied by Labsphere (Sutton, N.H.). The integrating sphere had three opening ports, one port for the input light (of 2.5 cm diameter), one at 90 degrees along a second axis as the detector port (of 2.5 cm diameter), and the third at 90 degrees along a third axis (i.e. orthogonal to the first two axes) as the sample port (of 5 cm diameter). A PR-650 Spectracolorimeter (same as above) was focused on the detector port at a distance of ~38 cm. The reflective efficiency of the integrating sphere was calculated using a calibrated reflectance standard from Labsphere having ~99% diffuse reflectance (SRT-99-050). The standard was calibrated by Labsphere and traceable to a NIST standard (SRS-99-020-REFL-51). The reflective efficiency of the integrating sphere was calculated as follows:

$$\text{Sphere brightness ratio} = 1/(1 - R\text{sphere} * R\text{standard})$$

The sphere brightness ratio in this case is the ratio of the luminance measured at the detector port with the reference sample covering the sample port divided by the luminance measured at the detector port with no sample covering the sample port. Knowing this brightness ratio and the reflectance of the calibrated standard (Rstandard), the reflective efficiency of the integrating sphere, Rsphere, can be calculated. This value is then used again in a similar equation to measure a sample's reflectance, in this case the PTFE light box:

$$\text{Sphere brightness ratio} = 1/(1 - R\text{sphere} * R\text{sample})$$

Here the sphere brightness ratio is measured as the ratio of the luminance at the detector with the sample at the sample port divided by the luminance measured without the sample. Since Rsphere is known from above, Rsample can be calculated. These reflectances were calculated at 4 nm wavelength intervals and reported as averages over the 400-700 nm wavelength range.

The single sheet gain is tested in the vertical (or perpendicular orientation relative to the front face of the diffuser boxed used in the E.T. Tester). In the horizontal, or crossed sheet configuration, the bottom sheet of the film stack is in the vertical orientation and the top sheet is horizontal or parallel to the front face of the diffuser box.

Table 1 as follows depicts the test results of the optical films prepared from Polymerizable Resin Compositions 1 and 2.

TABLE 1

| Polymerizable Resin Composition | Single Sheet Gain | Crossed Sheet Gain |
|---|---|---|
| 1 | 1.61 | 2.54 |
| 2 | 1.62 | 2.57 |
| 3 | 1.61 | 2.50 |
| 4 | 1.64 | 2.61 |

What is claimed is:

1. A triphenyl monomer having the general structure

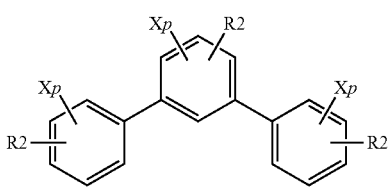

wherein X is independently halogen, aryl, or a $C_2$ to $C_{12}$ alkyl group;
p is 0 to 5; and
R2 is independently H or a substituent comprising a (meth)acrylate group and at least one R2 comprises a substituent comprising a (meth)acrylate group selected from i)

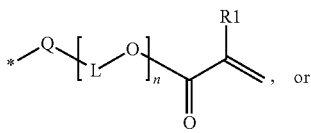, or ii)

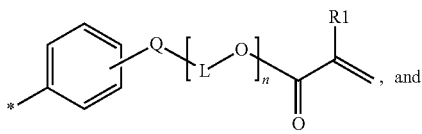, and wherein Q is O or S;
L is a $C_2$ to $C_6$ alkylene group optionally with a one or more hydroxyl groups;
n ranges from 1 to 10; and
R1 is H or $CH_3$;
wherein the triphenyl monomer is a mono(meth)acrylate monomer or tri(meth)acrylate monomer.

2. The triphenyl monomer of claim 1 wherein p is 0.
3. The triphenyl monomer of claim 1 wherein Q is O.
4. The triphenyl monomer according to claim 1 wherein the triphenyl monomer is a tri(meth)acrylate.
5. The triphenyl monomer according to claim 1 wherein the triphenyl monomer is a mono(meth)acrylate.
6. The triphenyl monomer according to claim 1 wherein Q is O, L is $C_2$ or $C_3$, and n is 1.
7. The triphenyl monomer of claim 6 wherein the triphenyl monomer has the structure

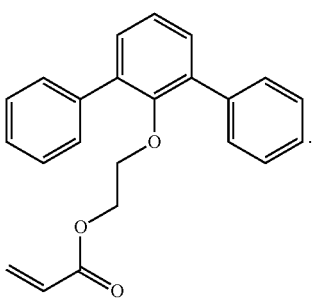 [SMILES: C=CC(=O)OCCOc1c(-c2ccccc2)cccc1-c1ccccc1]

8. A triphenyl monomer having the general structure

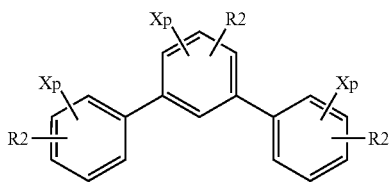

wherein X is independently halogen or a $C_2$ to $C_{12}$ alkyl group;
p is 0 to 5; and
R2 is independently H or a substituent comprising a (meth)acrylate group and at least one R2 comprises a substituent comprising a (meth)acrylate group selected from i)

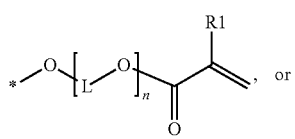, or ii)

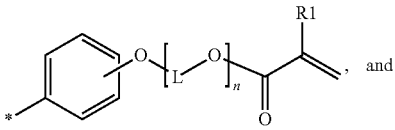, and wherein Q is O or S;
L is a $C_2$ to $C_6$ alkylene group optionally substituted with a one or more hydroxyl groups;
n ranges from 1 to 10; and
R1 is H or $CH_3$.

9. The triphenyl monomer of claim 8 wherein p is 0.
10. The triphenyl monomer of claim 8 wherein Q is O.
11. The triphenyl monomer according to claim 8 wherein the triphenyl monomer is a tri(meth)acrylate.
12. The triphenyl monomer according claim 8 wherein the triphenyl monomer is a di(meth)acrylate.
13. The triphenyl monomer according to claim 8 wherein the triphenyl monomer is a mono(meth)acrylate.
14. The triphenyl monomer according to claim 8 wherein Q is O, L is $C_2$ or $C_3$, and n is 1.
15. A UV curable polymerizable composition comprising the triphenyl monomer of claim 1 and a photoinitiator.
16. A UV curable polymerizable composition comprising the triphenyl monomer of claim 8 and a photoinitiator.
17. An optical film comprising a polymerized microstructured surface wherein the polymerized microstructured surface comprises the reaction product of the UV curable polymerizable composition of claim 15.
18. An optical film comprising a polymerized microstructured surface wherein the polymerized microstructured surface comprises the reaction product of the UV curable polymerizable composition of claim 16.
19. The optical film of claim 17 wherein the optical film is a brightness enhancing film.
20. The optical film of claim 18 wherein the optical film is a brightness enhancing film.

* * * * *